United States Patent
Chen et al.

(10) Patent No.: US 6,464,839 B1
(45) Date of Patent: *Oct. 15, 2002

(54) BETA-ELEMENE, METHOD TO PREPARE THE SAME AND USES THEREOF

(75) Inventors: Yuren Chen; Xiu Ying Wu, both of Dalian (CN)

(73) Assignee: Yuan da International Group Limited, Dalian (CN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,744

(22) PCT Filed: Apr. 13, 1998

(86) PCT No.: PCT/US98/07341

§ 371 (c)(1),
(2), (4) Date: Apr. 19, 2000

(87) PCT Pub. No.: WO98/46553

PCT Pub. Date: Oct. 22, 1998

(30) Foreign Application Priority Data

Apr. 14, 1997 (CN) .......................................... 97103910

(51) Int. Cl.$^7$ .......................... B01D 3/00; A01N 65/00; A61K 35/78

(52) U.S. Cl. ............................. 203/73; 203/39; 203/71; 424/725; 424/766

(58) Field of Search .............................. 424/195.1, 409, 424/725, 766; 514/919, 739, 703, 698, 409; 203/73, 71, 39

(56) References Cited

FOREIGN PATENT DOCUMENTS

CN          98106848          4/1998

OTHER PUBLICATIONS

Brewer et al. Experimental Techniques in Biochemistry, 1974.*
Hiroi, M. Sesquiterpenoids In The Leaf Oil Of Camphor Trees. II. Sesquiterpenoids Of Safrole Trees And Sesquiterpene Trees; Bull. Chem. Soc. Jpn. vol. 40, No. 11 pp. 2689–2690, 1967.*
Bin, X. Recent Advances In Pharmacologic Study Of Natural Anticancer Agents In China; Mem. Inst. Oswaldo Cruz, Rio de Janeiro, vol. 86, Suppl. II 51–54, 1991.*
Beijing Economic Information Center http://www.exin.net/ patent with Chinese Patent Abstract Database. Search report for Chinese Patent No. 98106848.0 Filed on Apr. 13, 1998. website and database hosted by Beijing Economic Information Center.

Patent Cooperation Treaty The International Search Report on Aug. 20, 1998. International application No. PCT/US98/07341. U.S. Ser. No. 09/402,744. International Filing Date Apr. 13, 1998.
Kozmin, Sergey A. et al. Asymmetric Diels–Alder Reactions of Chiral 1–Amino–3–siloxy–1, 3–butadine, Application to the Enantioselective Synthesis of (--)-. alpha. –Elemene.J. Am. Chem. Soc. 1997, vol. 119, No. 30, pp. 7165–7166.
Lai, Qian, Allergic reaction induced by thoracic cavity injection of elemene emulsion. Zhongliu Yanjiu Yu Linchuang 1996, 8(2). 143 Abs Only.
Li, Cuilan et al. Observation on the effect of combined elemene emulsion with chemical therapy in treatment of malignant ascites. Zhongguo Zhongxiyi Jiehe Zazhi 1996, 16(9).565–566 ABS. Only.
Li Qingmin et al. Quantitative determination of effective constituents of elemene injection. Shenyang Yaoke Daxue Xuebao 1997, 14(2). 118–119 ABS. Only.
Li, Qizhong et al. Elemene for cure and prevention of recurrence of bladder tumors. Chinese Journal of Clinical Oncology 1996, 23(9). 676–677 ABS. Only.
Liu, Naifu et al. An observation of effective intra abdominal cavity injection of elemene for treatment of ascites caused by oophoroma. Chinese Journal of Clinical Oncology 1996, 23(11). 832–833 Abs. Only.
Liu, Yanzhu et al. Elemene in treating of 15 cases of primary hapatocarcinoma. Fujian Yiyao Zazhi 1996, 18(4). 92–93 Abs. Only.
Liu, Yujun et al. MTT method for the study of elemene emulsion upon bladder cancer cell $T_{24}$, in vitro. Shanghai Yike Daxue Xuebao 1997, 24(2). 127–129 Abs. Only.
Long, Wei, Elemene emulsion in treatment of malignant hydrothorax and ascites, 28 cases. Hengyang Yixueyuan Xuebao 1996, 24(4). 303–304 Abs Only.
Lou, Jiangang et al. Effect of elemene on the erythrocyte immune function in patients with malignant tumors. Qingdao, Yixueyuan Xuebao 1997, 33(1). 46–47 Abs. Only.
Lu, Jiezhen et al. Intra intestinal use of elemene emulsion in treating malignant tumor in abdominal cavity. Fujian Yiyao Zazhi 1996, 18(3). 87–88 Abs Only.
Guo, Yongdian et al. Elemene from volatile oil of *C. wenyujin*, separation and determination. Chung Yao Tung Pao 1983, 8(3). 31 Abs. Only.
Harada, K. et al. Studies on the feeding attractants for fishes and shellfishes. 16. Probable feeding attractants in allspice *Pimenta officinalis* for black abalone *Haliotis discus*. Aquaculture, vol. 140, No. 1–2, pp. 99–108, 1996.

(List continued on next page.)

Primary Examiner—Jon P. Weber
Assistant Examiner—Patricia Patten
(74) Attorney, Agent, or Firm—Albert Wai-Kit Chan; Mark Elkins

(57) ABSTRACT

This invention provides an anti-cancer composition of high purity beta-elemene extracted from plant sources. This invention also provides for the use of the composition as well as a low cost method to prepare it by multiple passes through the precision distillation tower.

12 Claims, No Drawings

OTHER PUBLICATIONS

Hiroi, M. Sesquiterpenoids in the leaf oil of Camphor Trees. II. Sesquiterpenoids of safrole trees and Sesquiterpene Trees. Bull. Chem. Soc. Jpn. Nov. 1967, vol. 40, No. 11, pp. 2689–2690.

Hong, Wanjun. Treatment in 21 cases of carcinoma caused dropsy thoracic and abdominal cavity. Gynecology Department, Tumor Hospital, Chinese Academy of Medical Science (Abstract, full article in Chinese) Abs. Only.

Huang, Liming et al. Effect of element in malignant ascites of different king. Hunan Yixue 1996, 13(4). 241 Abs. Only.

Jelen HH. et al. Production of volatile sesquiterpenes by *Fusarium sambucinum* strains with different abilities to synthesize trichothecenes. Applied and Environmental Microbiology [Appl. Environ. Microbiol.] (United States), vol. 61, No. 11, pp. 3815–3820, 1995.

Jiang, Youjuan et al. Elemene plus cisplatimum diaminodichloride injection after thoracic cavity closed drainage. Jiangsu Yiyao 1997, 23(3). 218–219 Abs. Only.

Jusheng, H. Elemene in the treatment of primary brain tumors. Proc. Inc. Cancer Congr. Free Pap. 1994, vol. 2, pp. 877–879.

Kallio, H. et al. Maritime influence on the volatile terpenes in the berries of different ecotypes of juniper (*Juniperus communis* L.) in Finland. Journal of Agricultural and Food Chemistry [J. Agric. Food Chem.], vol. 37, No. 4, pp. 1013–1016, 1989.

Kao, Jun et al. Clinical study: HBO plus Element emulsion in treatment of late stage lung cancers. Chinese Journal of Clinical Oncology 1996, 23(8). 603–604 Abs. Only.

Kekelidze, NA. et al. Analysis of terpene variation in leaves and fruits of *Citrus unshiu* Marc. during ontogenesis. Flavour and Fragrance Journal [Flavour Fragrance J.]; vol.4, No. 1, pp. 37–41, 1989.

De Kraker JW, et al. (+)– Germacrene A biosynthesis. The committed step in the biosynthesis of the biosynthesis of bitter sesquiterpene lactones in chicory. Plant Physiol. Aug. 1998; 117(4): 1381–92 (Abstract).

De la Puerta R. et al. Antibacterial activity and composition of the volatile oil from *Achillea ageratum* L. Phytotherapy Research (United Kingdom), 1996, 10/3 (248–250).

de Morais, SMaia. et al. Essential oil of *Acanthospermum australe* DC. Journal of Essential Oil Research [J. Essent. Oil Res.], vol. 9, No. 5, pp. 601–602, Oct. 1997.

Dong, Zhonglian et al. Element with chemotherapy in treatment of malignant pleural effusion. Hunan Yixue 1996, 13(5). 307 Abs. Only.

Everaerts, C. et al. Sesquiterpenes in the frontal gland secretions of nasute soldier termites from New Guinea. Journal of Chemical Ecology [J. Chem. Ecol.], vol. 19, No. 12, pp. 2865–2879, 1993.

Fiorini, C. et al. Composition of the flower, leaf and stem essential oils from *Laurus nobilis* L. Flavour and Fragrance Journal [Flavor Fragrance J.], vol. 12, No. 2, pp. 91–93, Apr. 1997.

Fu, Naiwu et al. Anti–cancer action of β–Elemene and studies in pharmacology. Chung Yao tung Pao. May 1984, 9(2). 83–87 Abs. Only.

Gao. Tongjun et al. Element in treatment of 65 cases of malignant pleural effusion. Jiehebing Yu Xiongbu Zhongliu 1996, (1). 18–20 Abs. Only.

Gaydou, EM. et al. Sesquiterpene composition of basil oil. Assignment of the super(1)H and super(13)C NMR spectra of beta –elemene with two–dimensional NMR. Journal of Agricultural and Food Chemistry [J. Agric. Food Chem.], vol. 37, No. 4, pp. 1032–1037, 1989.

Gbolade, AA. et al. Volatile constituents from parsley cultures. Flavor Fragrance J., vol. 4, No. 2, pp. 69–71, 1989.

Gopichand Y, et al. Further studies of the terpenoid content in the gorgonian *Eunicea succinea*: 12, 13–bisepieupalmerin, a new cembranolide. J Nat Prod. Jul.–Aug. 1984; 47(4): 607–14 (Abstract).

Lu, Li et al. 13 and 14–alcoxide of β–elemene, separation and structural determination. Dalian Qinggongye Xueyuan Xuebao 1989, 8(3). 47–49 Abs. Only.

Lu, Liqin et al. Elemene emulsion artery injection in treatment of lung cancer. Zhejiang Zhongliu 1996, 2(3). 185 ABS. Only.

Lu, Qun et al. Elemene emulsion inhabits coagulation of rat's blood platelet. Suzhou Yixueyuan Xuebao 1996, 16(5). 844–846 ABS. Only.

Luo, Zhenzhu. Observation in clinical practice: Elemene for Malignant Tumors (cases report) and Medical images showing effectiveness of Elemene Treatment. Brain Surgery, East Angangtie Hospital (Abstract, full article in Chinese) ABS. Only.

Ma, Xiang et al. Research on prevention of proliferative Vitreoretinopathy: laboratory study on inhibitive effect of elemene plus dexamethasone to fibroblast. Zhongguo Shiyong Yanke Zazhi 1996, 14(9). 543–546 ABS. Only.

Mao, Guoxin et al. Treatment of malignant pleural effusion in lung cancer with elemene emulsion. Chinese Journey of Clinical Oncology. 1996, 23(1). 73–74 Abs. Only.

Njoroge, SM. et al. Japanese sour Citrus fruits. Part III. Volatile constituents of sudachi and mochiyuzu oils. Flavour and Fragrance Journal [Flavour Fragrance J.], vol. 10, No. 6, pp. 341–347, 1995.

Njoroge, SM. et al. Volatile components of the essential oils from Kabosu, daidai, and yuko, Japanese sour Citrus fruits. Flavour and Fragrance Journal [Flavour Fragrance J.], vol. 9, No. 6, pp. 289–297, 1994.

Pan, Qunxiong et al. Clinical effects of elements emulsion retention–enema in rectal cancer. Hunan Yixue 1996, 13(5). 306 ABS. Only.

Pelissier, Yves. et al. Volatile components of *Annona squamosa* L. Journal of Essential Oil Research [J Essent Oil Res], vol. 5, No. 5, pp. 557–560, 1993.

Pino, JA. et al. Composition of the essential oil of *Ocimum tenuiflorum* L. grown in Cuba. Journal of Essential Oil Research [J. Essent. Oil Res.], vol. 10, No. 4, pp. 437–438, Aug. 1998.

Qian, Jun et al. New drug for cancer: elemene, the pharmacology and clinical use. Chinese Journal of Clinical Oncology 1996, 23(6). 453–455.

Qin, Shukui et al. Elemene emulsion for advanced lung cancer (Meeting abstract). Cancer Conference 12th Asia Pacific, p. 298. Singapore, Oct. 17–20, 1995 (Meeting abstract) ABS. Only.

Qin, Shukui et al. Clinical study for Elemene emulsion on metastatic carcinoma of bone. Zhongliu Fangzhi Yanjiu 1997, 24(1). 51–53 ABS Only.

Qin, Shukui et al. Clinical study of elemene emulsion for treatment of metastatic carcinoma of bone. Chinese Journal of Clinical Oncology 1996, 23(5). 360–361 ABS. Only.

Rao, ChB. et al. A new lobane diterpene from an alcyonarian of Sclerophytum species of the Indian Ocean. Indian Journal of Chemistry. Section B. Organic including medicinal. New Delhi [Indian J. Chem. (B Org. Med.)], vol. 29, No. 7, pp. 681–682, 1990.

Raju B.L. et al. Two new oxygenated lobanes from a soft coral of Lobophytum species of the Andaman and Nicobar coasts. J. Nat. Prod. Lloydia (United States), 1993, 56/6 (961–966).

Rodriguez A.D. The natural products chemistry of West Indian gorgonian octocorals. Tetrahedron (United Kingdom), 1995, 51/16 (4571–4618).

Ruberto, G. et al. Composition of the essential oil from the bark of *Fagara macrophylla*. Journal of Essential Oil Research [J. Essent. Oil Res.], vol. 10, No. 4, pp. 443–445, Aug. 1998.

Scora, RW. et al. Leaf oils of two new avocado varieties endemic to Costa Rica. Journal of Essential Oil Research [J. Essent. Oil Res.], vol. 10, No. 6, pp. 705–707, Dec. 1998.

Shen, Qingle et al. Blood SOD, MDA, LPO, GSH changes during elemene emulsion treatment. Fujian Yiyao Zazhi 1996, 18(6). 79–80 ABS. Only.

Shen, Ziyun et al. Elemene emulsion in treatment of malignant tumors in their late stage. Chinese journal of clinical oncology 1997, 24(2). 141–142 ABS. Only.

Shi, Guangxia et al. Reports on laboratory research on β–elemene's effect against tumors; β–elemene's direct effect on leukemia cell L615 ABS. Only. Dalian Yixueyuan Xuebao 1994, 16(2). 137–140.

Shi J. Experimental pharmacological studies on the volatile oil of Wen–E–Zhu (Curcuma Aromatica Salisb.): Study on the Antitumor activity of beta–elemene. Zhongyao Tongbao; 6(6): 32–33 1981 (Abstract).

Su, Jingyu et al. New chemical from clavularia viridis shows certain anti–tumor effects. Kexue Tongbao 1996, 41(17). 1579–1582.

Su, Mei et al. Clinical Study in 22 Cases of Carcinoma caused Dropsy Thoracic and Abdominal Cavities and Superficial Metastasis. Beijing Hospital, Chinese Department of Health (Abstract, full article in Chinese) ABS. Only.

Sun, Peitong. Report on malignant tumors that are treated other than Elemene (30 cases) (Abstract, full article in Chinese) ABS. Only.

Tao, Shudong et al. 30 cases of late staged malignant tumor around cervical area under treatment of elemene. Chinese Journal of Clinical Oncology 1996, 23(3). 225–226.

Tazerouti, F. et al. Analysis of essential oils from *Pinus halepensis* Mill. needles using gas chromatography and mass spectrometry. Plant. Med. Phytother (France), 1993, 26/3 (161–176) No Translation.

Thoppil J.E. Essential oil composition of *Moschosma polyhstachya* (L). Indian Journal of Pharmaceutical Sciences (India), 1997, 59/4 (191–192).

Yaghmai, MS. Volatile constituents of *Scutellaria lateriflora* L.. Flavour and Fragrance Journal [Flavour Fragrance J.], vol. 3, No. 2, pp. 27–31, 1988.

Wang, Baocheng. Experiment on elemene emulsion's effects on drug–resistant tumor cells. Chinese Journey of Clinical Oncology. 1996, 23(2). 143–146 Abs. Only.

Wang, J. et al. Phase III clinical trial of elemenum emulsion in the management of malignant pleural and peritoneal effusions. Chung Hua Chung Liu Tsa Chih, 18(6):464–7 1996 (Abstract) ABS. Only.

Wang, Jinwan et al. Injection of Elemene Emulsion, A Phase II Clinical Trial. Chinese Academy of Medical Science, Beijing Tumor Hospital (Abstract, full article in Chinese) ABS Only.

Wang, Jinwan et al. Elemene emulsion in treatment of malignant hydrothorax and ascites, Phase III clinical observation. Chinese Journal of Clinical Oncology 1996, 23(4). 301–304.

Wang, Pinghui et al. High dose elemene plus AP (LxAP) for haptic artery infusion in treatment of hapatocarcinoma. Chinese Journal of Clinical Oncology 1997, 24(1). 69–70 ABS. Only.

Wu, Xiaocui et al. Elemene plus radiotherapy in middle and late stage malignant tumors. Zhongguo Zhongliu Linchuang Yu Kangfu 1996, 3(2). 47–49 ABS. Only.

Xiao, Lisen et al. Sensitivity of human cancer cell to elemene: MTT method. Chinese Journal of Clinical Oncology 1996, 23(3). 223–224 ABS. Only.

Xiao, Lisen et al. Clinical research: elemene by haptic artery infusion in treating primary haptic carcinomas. Chinese Journal of Clinical Oncology 1996, 23(10). 757–760 ABS. Only.

Xu, Bin. Recent advances in Pharmacologic study of natural anticancer agents in china. Mem Inst. Oswaldo Cruz, 86 Suppl 2:51–4 1991.

Xu, Hongsheng et al. Effect of elemene on SOD activity in blood serum of patients of brain tumors. Chinese Journal of Clinical Oncology 1996, 23(7). 527–529 ABS. Only.

Xu, Jiazhang et al. Elemene Emulsion Treatment of Dropsy Thoracic Cavity in Patients with Terminal Carcinomas, A result of Phase II Clinical Trial. Beijing Thoracic Tumor Institute and Hospital (Abstract, full article in Chinese) ABS. Only.

Xu, Yanghui et al. Preliminary Study of Elemene Carotid Artery Infusion in Treatment of Intracranial Metastasis. Dept. Neurosurgery, Second Subsidiary Hospital, Dalian Medical College (Abstract, full article in Chinese) ABS. Only.

Yan, Jianli. Elemene, the anti–tumor drug, method for intravenous administration in subclavan vein. Hunan Yixue 1996, 13(3). 168 ABS. Only.

Yang, H. et al. The antitumor activity of elemene is associated with apoptosis. Chinese Journal of Oncology (China), 1996, 18/3 (169–172) Abs. Only.

Yang, Jijun et al. Handling with the phlebitis caused by element injection with Sugaojieliao Ointment. Fujian Yiyao Zazhi 1996, 18(4). 96–97.

Yin Z. –M. et al. Elemene plus fluorouracil in the treatment of advanced gastric cancer. Chinese Journal of Clinical Oncology (China), 1996, 23/11 (810–812) Abs. Only.

Zoghbi, Maria das GB. et al. Volatile constituents from leaves and stems of Protiumheptaphyllum (Aubl.) Mar., Journal of Essential Oil Research [J Essent Oil Res], vol. 7, No. 5, pp. 541–543, 1995.

Zhang, Li et al. Elemene emulsion in treatment of malignant pleural effusion, 46 cases. Henan Zhongliuxue Zazhi 1996, 9(4). 267 Abs Only.

Zhang, Wanling. New anti–tumor drug– elemene emulsion in treatment of malignant pleural effusion, phase II. Chinese Journey of Clinical Oncology. 1996, 23(1). 75 Abs. Only.

Zhang, Weiliang et al. Abdominal cavity injeciton of elemene intreatment of malignant dropsy abdominal cavity. Chinese journal of clinical oncology 1997, 24(2). 155–156 Abs. Only.

Zhang, Yinghong et al. method of elemene injection duct in subclavian vein may effectively avoid phlebitis. Chinese Journal of Clinical Oncology 1996, 23(5). 361–363 Abs. Only.

Zhao, Fuzhi et al. Elemene Emulsion in Treatment of Malignant Dropsy Abdominal Cavity. Chinese Journal of Clinical Oncology 1996, 23(12). 902 Abs. Only.

Zhao, Yajun et al. Observation in elemene emulsion thoracic cavity injection in treatment of malignant hydrothorax. Shiyong Zhongliuxue Zazhi 1996, 10(2). 52,80 Abs. Only.

Zhong, Yongxiang et al. Preclinical study of pharmacology of elemene and its clinical uses. Hunan Yixue 1996, 13(2). 119–120.

Zhu, Lujia et al. Effect of elemene emulsion on hemorheology of acute blood stagnation in rats. Zhongguo Yiesheng Zhiwu Ziyuan 1996, (3). 6–8 Abs. Only.

Azzouz, M. A. et al. Comparison between cold–pressed and distilled lime oils through the application of gas chromatography and mass spectrometry. J. Food Sci. 1976, vol. 41, pp. 324–328.

Sergey A. Kozmin et al. Asymeetric Diels–Alder reation of chiral 1– amino–3–siloxy–1,3–butadiene: applocation to the enantioselective synthesis of (–)–a–elemene. J. Am. Chem. Soc. 1997, 119, 7165–7166.

Sergey A. Kozmin et al.

S. Khetwal et al. Xanthones from swertia alata. Indian Journal of Pharmaceutical Sciences. Jul.–Aug. 1997.

Chen, Yuheng. Preliminary studies on Chinese Curcuma indetification of the plants. Abstract is on the last page of article. Yaoxue May 1981 385–389 Abs Only.

Cheng, Biqiang et al. Plants Rosources and Utilization from Six Species Of Cymbopogon Plant. Abstract is on the page article Xiangliao, Xiangjing, Huazhuangpin, China 1994 Abs Only.

Mitsuo Takahashi et al. Study on the components of Panax Ginseng C.A. Myser II. On the Etheral Extract of ginseng radix Alba.(2) Yakugaku Zasshi 84(8) 752–756 Abs Only.

Afsharypuor S. et al. Volatile constituents of *Origanum vulgare* ssp. viride from (syn. *O. heracleoticum*) from Iran. Planta Medica (Germany), 1997, 63/2 (179–180).

Anjaneyulu, V. et al. Two new norlobane diterpenes from a soft coral *Lobophytum pauciflorum* of the Indian Ocean. Indian J. Chem. (B Org. Med. Chem.), vol. 32, No. 11, pp. 1198–1199, 1993.

Anjaneyulu, ASR. et al. A new lobane diterpene acid from the soft coral *Lobophytum microlobulatum* of the Andaman and Nicobar Islands. Indian Journal of Chemistry. Section B. Orgnaic including medicinal. New Delhi [Indian J. Chem. (B Org. Med.)], vol. 35, No. 1, pp. 45–48, 1996.

Anjaneyulu, ASR. et al. Two new lobane derivatives from the soft coral *Lobophytum pauciflorum* of the Havelock Island of the Indian Ocean. Indian Journal of Chemistry. Section B. Organic including medicinal. New Delhi [Indian J. Chem. (B Org. Med.)], vol. 34, No. 12, pp. 1074–1079, 1995.

Anjaneyulu, V. et al. Isolation of loba–8, 10, 15–triene–13, 17, 18–triol–17, 18–diacetate from a soft coral of Lobophytum species of the Andaman and Nicobar Islands. Indian Journal of Chemistry. Section B. Organic including medicinal. New Delhi [Indian J. Chem. (B Org. Med.)], vol. 34, No. 12, pp. 1071–1073, 1995.

Anjaneyulu, V. et al. Two new norlobane diterpenes from a soft coral lobophytum pauciflorum of the Indian ocean. Indian Journal of Chemistry vol. 32B. Nov. 1993, pp. 1198–1199.

Asres K. et al. Terpenoid Composition of the wound–induced bark exudates of *Commiphora tenius*from Ethiopia. Planta Med. Jun. 1998 ;64(5): 473–5.

Bamba D. et al. Essential oil of *Eupatorium odoratum*. Planta Med. (Germany), 1993, 59/2 (184–185).

Brophy, JJ. Constituents of the volatile leaf oils of *Polyscias fruticosa* (L.) harms. Flavour and Fragrance Journal [Flavour Fragrance J.], vol. 5, No. 3, pp. 179–182, 1990.

Brum R.L. et al. Antibacterial activity of Cochlospermum regium essential oil. Fitoterapia (Italy), 997, 68/1 (79).

Chalier, P. et al. Production of volatile components by *Penicillium roqueforti*cultivated in the presence of soya bean oil. Flavour and Fragrance Journal [Flavour Fragrance J.], vol. 8, No. 1, pp. 43–49, 1993.

Chen, Jianqun et al. effects of element injection on subgroup lymph cells in peripheral circulation. Chinese Journal of Clinical Oncology 1996, 23(4). 229–301 Abs. Only.

Chen, Naijie et al. Treatment of 43 cases of primary haptic carcinoma with elemene emulsion. Fujian Yiyao Zazhi 1996, 18(5). 79–80 Abs. Only.

Chinou I.B. et al. Chemical and antibacterial studies of two Helichrysum species of Greek origin. Planta Med (Germany), Apr. 1997, 63 (2) p181–3.

* cited by examiner

BETA-ELEMENE, METHOD TO PREPARE THE SAME AND USES THEREOF

This is a 371 of PCT/US98/07341, Filed Apr. 11, 1998, which claims priority of Chinese patent application No. 97103910.0, Filed Apr. 14, 1997, the content of which are incorporated here into this application.

Throughout this application, various publications are referenced and full citations for these publications may be found in the text where they are referenced. The disclosures of these publications are hereby incorporated by reference into this application in order to more fully describe the state of the art as known too the skilled therein as of the date of the invention described and claimed herein.

BACKGROUND OF THE INVENTION

Beta-elemene is a chemical compound that can be extracted from numerous plants. Curcuma Wenyujin Chen et C. Ling, Curcuma aromatia, and Curcuma longa linn (all belonging to Ziniberaceae) are resources for elemene extraction in China. They grow in tropical areas around the world. In China they are found primarily in Guangdong, Sichuan Fujian, Guangxi and Zhejiang provinces. More than 50 different plants have been found to contain beta-elemene, such as Radix Inulae, Radix Ginseng, E. Wenyujin chen et C. Ling and others.

Beta-elemene can be extracted from the essential oil contained in plants. In China, about 40 different essences were found to contain more than 1% beta-elemene. Higher concentrations are found in the essential oil produced from *Magnolia sieboldii, Citrus junos* leaves and *Aglaia odorata* flower and particularly, *G. Cymbopogon winterianus* Jowitt.

*G. Cymbopogon winterianus* Jowitt is one of the major plant resources for essential oil production in China. The essential oil contains 1.63-5.21% of beta-elemene and the byproduct of essence extraction i.e. crude product, contains as much as 80% beta-elemene.

Currently China produces more than 2000 tons of oil extracted from the *G. Cymbopogon winterianus* Jowitt annually. This production is over 50% of the world total, and it is one of the major essential oil exports for China. *G. Cymbopogon winterianus* Jowitt provides a rich resource from which large quantities of beta-elemene can be extracted economically.

Beta-elemene has the chemical name:

1-methyl-1-vinyl-2,4-diisoprotenyl-cyclohexane.

Beta-elemene is found in elemene in the various extracts, along with gamma and delta elemene, which are chemical isomers of the beta-elemene. The extracts contain other compounds as well and it is very difficult to isolate beta-elemene from these other compounds using routine isolation techniques.

Preparations made from Curcuma *Aromatica Salisb* (which contains elemene) have been a part of Chinese herbal remedies for centuries. It has been used internally and topically for a wide variety of ailments.

Elemene at various concentrations with other ingredients appears in applications as diverse as a mosquito repellent (see U.S. Pat. No. 5,66,781), burn treatment (see U.S. Pat. Nos. 5,558,914 and 5,384,125) and treatment for Herpes Simplex (see U.S. Pat. No. 5,385,733).

Of particular interest is the anti-tumor characteristics exhibited by elemene.

Yang, H., Wang, X. and Yu, L, Journal article—NHI database ID# 98048492—"THE ANTITUMOR ACTIVITY OF ELEMENE IS ASSOCIATED WITH APOPTOSIS" Chung Hua Chung Liu Tsa Chih;18(3) :169–72 1996, Cancer Institute, Zhejiang Medical university, Hangzhou, China determined that the anti-tumor activity of elemene is associated with cell cycle arrest from S to G2M phase transition and with the induction of apoptosis. They further demonstrated this effect in vitro and in vivo to human and murine tumor cells.

All purity and concentration values in this application are reported by volume. The concentration % in a sample is the volume of beta-elemene divided by the total volume of the sample, multiplied by 100.

Guo,Y T. Journal article—NIH data base ID# 83285582—"ISOLATION AND IDENTIFICATION OF ELEMENE FROM THE ESSENTIAL OIL OF CURCUMA WENYUJIN", Chung Yao Tung Pao; 8(3):31 1983)(the present inventors were co-authors of this paper) described the isolation of elemene from Curcuma Wenyujin and described elemene's anti-neoplastic activities. Beta-elemene in a concentration of 92% was used. The beta-elemene was extracted using chromatography.

Wang J., Zhang H,, and Sun, Y. Clinical trial-Journal article—NIH data base ID#98048551—PHASE III CLINICAL TRIAL OF ELEMENUM EMULSION IN THE MANAGEMENT OF MALIGNANT PLEURAL AND PERITONEAL EFFUSIONS" reported the use of elemene emulsion in the management of malignant effusions.

Shi, J. Journal article—NHI data base ID # 82631581— "Experimental pharmacological studies on the volatile oil of Wen-E-Zhu (Curcuma Aromatica Salisb): Study on the anti-tumor activity of beta-elemene" —Zhongyao Tongbao, Luda Inst. Medical and Pharmaceutical Sciences, Luda, P.R.China demonstrated that the beta-elemene component of elemene exhibited marked anti-tumor activity against murine Ehrlich ascites carcinoma and rat ascitic reticulum cell sarcoma. Diarrhea and weight loss were reported as side effects during treatment. The material used contained beta-elemene 65%, gamma and delta-elemene 20%, and impurities 15%. The beta-elemene was extracted by chromatography.

Fu, N. W. Journal article—NIH data base ID #84282970—"ANTITUMOR EFFECT AND PHARMACOLOGICAL ACTIONS OF BETA-ELEMENE ISOLATED FROM THE RHIZOME OF CURCUMA AROMATICA", Chung Yao Pao; 9(2) :35–9 1984 reported on the anti-tumor effect of beta-elemene, one of the monomers comprising the elemene isomer. As in Shi. J article above, the material used contained beta-elemene 65%, gamma and delta-elemene 20%, and impurities 15%.

In December 1993 elemene was designated as a Chinese national Class II new drug. In February 1994 the anti-cancer effect of elemene was confirmed by the health authority of the P.R. of China.

During the 2 year trial of the drug in China, it was determined that elemene has not only the ability to manage malignant chest and abdominal ascites, but also had beneficial effects on brain tumors (neuroglioma), liver and esophageal cancer.

The elemene has apparent anti-cancer activity on mouse Ehrlich Ascites Carcinoma (EAC) and mouse leukemia P388, $L_{1210}$, ARS and rat YAS etc. From the Chinese phase I, II and III clinical trials, it was proved that the elemene exhibits some control over cancerous chest and abdominal ascites and surface tumors. The total effect rate was about 69%. It should be noted that 27% of the cerebral carcinoma patients reached CR level with a combination of the elemene and local chemotherapy in the expanded clinical trials.

SUMMARY OF THE INVENTION

The research conducted demonstrated that the beta-elemene component of elemene had significant anti-tumor characteristics and that the primary mechanism was the induction of apoptosis in the tumor cells.

Previous researchers produced beta-elemene by chromatography, which produced only small quantities of beta-elemene at high cost. The maximum purity attained had been 92%.

In addition, work performed in the Department of Embryology of the Dalian Medical University revealed that beta-elemene is able to pass through the brain-blood barrier (BBB) and thus reach tumors within the brain.

It is an object of the present invention to provide for an anti-cancer drug wherein the active ingredient is beta-elemene.

This invention relates generally to compositions of beta-elemene and method of producing higher concentration than previously possible, produced at reasonable cost using abundant plant sources; pharmaceuticals containing beta-elemene and application of the pharmaceuticals to treat various malignant diseases.

Since indications for the pharmaceutical composition of beta-elemene at the present time are mainly for malignant disorders it is an object of the invention to provide a method for applying the pharmaceutical to treat various malignancies, especially neuroglioma and solid tumors.

Having identified the beta-elemene monomer as a component of elemene with a strong anti-tumor activity, it is a purpose of the present invention to provide for a method to produce it in quantity and with sufficient purity to reduce the side effects from any impurities, and provide a standard dosage. As a result, the governmental requirements for pharmaceuticals with respect to analytical definition and reproducible composition, independent from the variable composition of the starting material from any of several plants can be fulfilled.

A further object of the invention is to provide a beta-elemene composition of high concentration (96.4–97.2%). A composition with highly concentrated effective content and minimum impurities is required in many countries with high pharmaceutical standards which are not usually met by simple extracts since the norms apply to pure substances. Until now it has not been possible to prepare such high concentrations of beta-elemene from the plant sources.

Another advantage of the highly concentrated bete-elemene is the reduced amount that must be dosed to be effective.

An additional advantage of highly concentrated beta-elemene is the further removal of inactive substances. The extensive removal of inactive accompanying substances enhances the safety of the pharmaceutical, since the simpler composition of the active component concentrate facilitates a more precise analytical determination of the main components and detection of potential impurities.

It is a further object of the invention to provide a delivery means for effective levels of the beta-elemene to reach surface and internal tumors.

It is a further object of the invention to provide a low-cost high-volume means of production of beta-elemene.

The present invention is the use and preparation of beta-elemene that is characterized by a purity of more than 96%. The invention involves the preparation methods and the composition of an anti-cancer drug, especially with the preparation methods and the composition of an anti-cancer drug in which the beta-elemene is the effective ingredient.

DETAILED DESCRIPTION OF THE INVENTION

China produces 2000 tons of oil extracted from *G. Cymbopogon winterianus* Jowitt. The oil contains 1.63–5.21% beta-elemene. In the process of extracting the oil for its essence a by-product, called "crude product", is produced. This crude product has a higher concentration of beta-elemene than the original plant material, as high as about 80%. This crude product provides an inexpensive, abundant source of feed material for this new process.

This invention provides a composition of 96.4–97.2% beta-elemene.

The other ingredients are

| | |
|---|---|
| gamma-elemene | 0.5% |
| elemenol | 0.8–1.2% |
| Copane | 1.3–1.7% |
| Isofuranogermacrene approx. | 0.2% |

This invention provides a composition of at least 96.4% beta-elemene.

This invention provides the above compositions having components extracted from a group of over 40 plants known to have useful levels of beta-elemene.

This invention provides an injectable formulation containing the above compositions. The injectable formulation may then be administered to the subject via different routes, such as intravenous injection, intramuscular injection, intradermal injection, peritoneal injection and injection into solid tumor.

This invention provides the above compositions that can be added into cream, ointments or presence in raw materials to prepare the same.

This invention provides a method for obtaining a beta-elemene composition using a distillation tower to separate the crude material into fractions, the tower being specifically constructed (the precision distillation tower) to produce beta-elemene at a concentration of 96.4–97.2% and at very low cost.

This is the first time that the precision distillation tower is used to produce beta-elemene. It is achieved through the multi-fractionation of the crude material in the precision distillation tower.

The precision distillation tower to be used is designed and manufactured specifically for this purpose. A tower has a height of 1.4 meters, a tower diameter of 6 cm and the tower interior is fitted with as many 3×3 mm hollow 120 mesh stainless steel cylinders as can be fit within it. The number of plates within the tower is 40.

This invention utilizes at least one of the following as the source of the plant material: *G. Cymbopogon winterianus* Jowitt, *zhangzhou Aglaia odorata* flower, *Fuzhou Aglaia odorata* flower, *Chunging Aglaia odorata* flower, *Chunging Aglaia odorata* leaves, *Zhangzhou Aglaia odorata* leaves, *Yibin geranium* leaves, *Kunmin geranium* leaves, *Litchi chenensis cinnamomifolium,* dry *Lauris nobilis, Citrus limona* leaves, *Vitis vinitera* grape leaves, *Clausena lansium* leaves, *Fortunella margarita* leaves, *Fortunella oborata,* C. Wenyujin Chen, and *Magnolia sieboldi.*

This invention provides for a method comprising the following steps:

(A) obtaining as a plant source at least one of the following plants: *G. Cymbopogon winterianus* Jowitt, *Zhangzhou Aglaia odorata* flower, *Fuzhou Aglaia odorata* flower, *Chunging Aglaia odorata* flower, *Chunging Aglaia odorata* leaves, *Zhangzhou Aglaia odorata* leaves, *Yibin geranium* leaves, *Kunmin geranium* leaves, *Litchi chenensis cinnamomifolium,* dry *Lauris nobilis, Citrus limona* leaves, *Vitis vinifera* grape leaves, *Clausena lansium* leaves, *Fortunella margarita* leaves, *Fortunella oborata,* C. Wenyujin Chen, and *Magnolia sieboldi.*

(B) extracting oil from said plant source to produce crude product;

(C) loading said crude product into the distillation tower to separate said crude product into fractions; and (D) collecting the fraction with the highest concentration of beta-elemene, thereby producing a composition with a concentration of about 95t beta elemene. The harvest rate for this fraction is about 63% of the input.

The beta-elemene composition produced in step (D) is further concentrated by a second fractionation comprising the following additional step:

(E) loading the composition comprising about 95% beta-elemene into the tower to separate into fractions; and collecting the fraction with the highest concentration of beta-elemene, thereby producing a composition of beta-elemene with a concentration of 96.4–97.2%. The harvest rate is about 60%.

In the preferred embodiment, this invention provides for the method of obtaining beta-elemene from its plant sources comprising the steps of:

The First Fractionation (a) Obtaining the crude product that is produced as a by-product of elemene essence extraction (such as by the Essence Chemical Factory-China);

(b) Loading 2000 g of crude product containing more than 80% beta-elemene into the precision distillation tower. The precision distillation tower has a height of 1.4 meters and a diameter of 6 cm. The tower cavity is fitted with as many hollow 3 mm×3 mm 120 mesh stainless steel cylinders as can be fit inside. The number of plates within the tower is 40;

(c) Establishing a vacuum of not less than 2 mmHG, usually between 2–5 mmHg with a temperature range from 86 to 93 degrees C. and a reaction time of about 10 hours. There are 3 different temperature ranges for fractionation; 86–88 degrees C., 89–90 degrees C. and 91–93 degrees C. The fraction of 89–90 degree C. has the highest concentration of beta-elemene and is collected. The harvest rate for the fraction of 89–90 degrees C. is about 63% of the input. The purity at this point is about 95%;

For the second fractionation (d) Take 2000 g of the fractionation previously collected from the first fractionation with a purity of 95% and repeat the process using the same parameters as the first fractionation. During the fractionation use 3 temperature ranges: 86–88 degrees C., 89–90 degrees C. and 91–93 degrees C. The fraction from the 89–90 degree C. range has the highest concentration of beta-elemene and is retained. The harvest rate for the second fractionation is 60% and the purity of the beta-elemene is 96.4–97.2%;

(e) The residue remaining in the tower and the fractions at 86–88 and 91–93 degrees C. can be further refined or recycled. Recycle the unused fractions from the first pass together with the remaining oil extract in the tower which went through two fractionations by loading the tower with these materials. Steps (a) through (d) are repeated and the fraction at 89–90 degrees C. is collected. The harvest rate is 20%.

If desired the fractionation can be repeated further, using these same steps.

The final product from the precision distillation contains:

| | |
|---|---|
| beta-elemene | 96.4–97.2% |
| copane | 1.3–1.7% |
| Elemenol | 0.8–1.2% |
| gamma-elemene | 0.5% |
| Isofuranogermacrene | 0.2% |

Beta- and gamma elemene have similar structure and anti-cancer activities.

Since the fractionation is conducted in a sealed container there is no environmental pollution.

The beta-elemene can be used in any pharmaceutically suitable carrier.

In the preferred embodiment, prepare the pharmacological preparation from the beta-elemene composition by the following steps:

(1) Mix the beta-elemene as obtained above with phosphatide and cholesterol, heat to 80 degrees C. until the mix melts down and becomes clear.

(2) Dissolve NaH2PO4 and Na2HPO4 in water and heat to 80 degrees C.

(3) Place the mixtures from above steps (1) and (2) into a high speed emulsifier until the mixtures become emulsive injection.

(4) Filtrate the emulsive injection through a G4 sintered glass funnel, and check the particle size.

(5) Fill the checked emulsive injection into ampules and seal them. Sterilize at 100 degrees C. for 40 minutes to yield the final product.

For the purposes of this invention "pharmaceutically suitable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Research Results

Using the described procedure to prepare the beta-elemene anti-cancer drug, the following results were obtained from animal pharmacodynamic studies:

(A) Ascites carcinoma: intra-peritoneal injection of the beta-elemene has a stable therapeutic effect on EAC and $S_{180}$ ascites cancer. The life prolongation rates are 85–310% and 90–321% respectively. The life prolongation rate for hepatic ascites carcinoma is 103–224%.

(B) Solid tumor; The beta-elemene injection has some inhibition effect on $S_{180}$ solid tumor. The inhibition rate is 33–59%. The inhibition rate for hepatic solid tumor is 10–30%.

(C) Murine leukemia $L_{1210}$: The beta-elemene injection has obvious therapeutic effect on $L_{1210}$ leukemia. The life prolongation rate was 47–289%.

(D) Neuroglioma: It was indicated in the pharmacodynamic study of cerebral neuroglioma using murine sub-renal capsule model that the inhibition rate was 50–70%.

(E) There was no measurable bone marrow inhibition or reduction of white blood cell count, etc which are common side effects of conventional anti-cancer drugs.

Based on the findings of these experiments, the inventors suggest that beta-elemene has beneficial effects on the treatment of ascites carcinoma, solid tumor, neuroglioma, murine leukemia etc. with no obvious side effects observed. They further conclude that beta-elemene was suitable for development as a national (China) class I new drug for human cancerous ascites, neuroglioma and solid tumor, and for research in its use to be continued.

Human Data

In two instances, patients at the Second Affiliated Hospital of the Dalian Medical University were treated with the beta-elemene composition as an emulsive injection. The medical records were kept at that hospital.

Patient I: (Hospitalization #3106) A 25 year old female Patient had headache, right side arm and leg weakness and hemiplegia. She was diagnosed by CT scan as having a thalamic glioblastoma. The tumor size was 3.8×5.3×4 cm. The patient was hospitalized for surgery in July 1995. 80% of the tumor was excised, but it grew back to the full size within two weeks after the operation. A beta-elemene emulsive injection was employed through 600 ml cervical artery intubation and 400 ml intravenous drip alternately once per day. The growth of the tumor was quickly controlled, but on CT scan there was no apparent reduction in tumor size. The patients symptoms improved and she survived for 11 months with the tumor.

Patient II: (Hospitalization Number 3679) A 65 year-old female

The patient had headache, vomiting and gait problems due to lung cancer. A CT scan indicated that the lung cancer had resulted in multiple metastasis to the brain. The tumor in the right cerebellum was 2.8×4.0×3.1 cm. The size of a tumor in the left ganglion basal zone was 0.5×1.5×1.6 cm. Due to the lung metastasis and the age of the patient, surgery was difficult to perform. The patient was hospitalized in mid November 1996.

It was estimated that she would not survive longer than a month. The patient was treated with beta-elemene as prepared herein. The patient received the same regimen as patient I. Her condition improved, the headache was reduced. The vomiting stopped. In the middle of December 1996 the patient had another CT scan. The size of the tumor was reduced. In March 1997 the patient requested to leave the hospital as the lung cancer spread to the rib and lymph nodes, along with the pathological left forearm fracture. The prolongation of the life of the patient was more than 4 months, based upon previous experience with patients at that stage of illness.

We claim:

1. A method for producing a composition containing beta-elemene from a plant source using a distillation tower comprising the following steps:

(a) obtaining said plant source;

(b) extracting oil from said plant source to produce a crude product;

(c) loading said crude product into a distillation tower to separate said crude product into fractions; and (d) collecting the fraction with the highest concentration of beta-element, thereby producing a composition of beta-elemene, wherein said tower has a height of 1.4 meters and a diameter of 6 cm; wherein said tower has an inside and outside surface, wherein said inside surface defines a cavity; and wherein said cavity is fitted with as many 3mm×3mm hollow 120 mesh stainless steel cylinders as will fit therein.

2. The method for producing a composition of beta-elemene according to claim 1 further comprising the steps:

(e) loading said tower with said fraction collected in step (d);

(f) drawing multiple fractions; and (g) collecting the fraction with the highest concentration of beta-elemene, thereby producing a composition of beta-elemene.

3. The method according to claims 1 or 2, wherein said plant source is at least one selected from the group consisting of *G. Cymbopogon winterianus* Jowitt, *Zhangzhou Aglaia odorata* flower, *Fuzhou Aglaia odorata* flower, *Chunging Aglaia odorata* flower, *Chunging Aglia odorata* leaves, *Zhangzhou Aglaia odorata* leaves, *Yibin geranium* leaves, *Kunmin geranium* leaves, *Litchi chenensis cinnamomifolium*, dry *Lauris nobilis*, *Citrus limona* leaves, *Vitis vinifera* grape leaves, *Clausena lansium* leaves, *Fortunella margarita* leaves, *Fortunella odorata*, C. Wenyunjin Chen, and *Magnolia sieboldi*.

4. The method for producing a composition of beta-elemene according to claim 3 further comprising the following steps:

(a) establishing a vacuum in said tower of 2–5 mmHg;

(b) heating said tower to a temperature range of 86–93° C.; and (c) using a reaction time of about 10 hours.

5. The method for producing a composition of beta-elemene according to claim 4 wherein said vacuum is 2 mmHg.

6. The method for producing a composition of beta-elemene according to claim 5 further comprising:

(a) a first fractination comprising the steps of:
producing a fraction at a temperature range of 86–88° C.;
producing a fraction at a temperature range of 89–90° C.;
producing a fraction at a temperature range of 91–93° C.;
collecting said fraction produced at said temperature range of 89–90° C. to obtain a first composition;
removing any residual material remaining in the tower; and (b) a second fractionation comprising the steps of loading said first composition produced at said temperature range of 89–90° C. into said tower;
producing a fraction at a temperature range of 86–88° C.;
producing a fraction at a temperature range of 89–90° C.;
producing a fraction at a temperature range of 91–93° C.; and
collecting said fraction produced at said temperature range of 89–90° C., to produce a second composition of beta-elemene.

7. The method of producing a composition of beta-elemente according to claim 6 further comprising loading the fractions collected at 86–88° C. and 91–93° C. into said tower and repeating the steps of claim 6.

8. The method according to claim 6 further comprising:
combining said fractions produced at said temperature ranges of 86–88 and 91–93° C. with the residue remaining after fractionation;
loading said tower with said combination; and
repeating the steps of claim 6.

9. The method for producing a composition of beta-elemene according to claim 6 wherein said plant source is *G. Cymbopogon winterianus* Jowitt.

10. The method for producing a composition of beta-elemene according to claim 9 wherein said composition of beta-elemene comprises at least 96% beta-elemene.

11. The method of producing a composition of beta-elemente accrding to claim 10 wherein said composition of beta-elemene comprises between 96.4 and 97.2% beta-elemene.

12. The method of producing a composition of beta-elemente accrding to claim 10
wherein said composition comprises:
about 96.4–97.2% beta-elemene;
about 0.8–1.2% elemenol;
about 1.3–17% copane;
about 0.5% gamma-elemene; and
about 0.2% isofuranogermacrene.

\* \* \* \* \*